United States Patent [19]
Chambers et al.

[11] Patent Number: 5,807,400
[45] Date of Patent: Sep. 15, 1998

[54] DEFORMABLE INTRAOCULAR LENS INSERTION SYSTEM

[75] Inventors: Thomas J. Chambers, Upland; Vladimir Feingold, Laguna Niguel; Daniel C. Eagles, Capistrano Beach, all of Calif.

[73] Assignee: Staar Surgical Company, Inc., Monrovia, Calif.

[21] Appl. No.: 401,523

[22] Filed: Mar. 10, 1995

Related U.S. Application Data

[63] Continuation-in-part of Ser. No. 345,360, Nov. 18, 1994, abandoned, which is a continuation-in-part of Ser. No. 240,520, Jul. 19, 1994, abandoned, which is a continuation-in-part of Ser. No. 221,013, Apr. 1, 1994, Pat. No. 5,494,484, which is a continuation-in-part of Ser. No. 220,999, Apr. 1, 1994, abandoned, which is a continuation-in-part of Ser. No. 197,604, Feb. 17, 1994, Pat. No. 5,499,987, which is a continuation-in-part of Ser. No. 196,855, Feb. 15, 1994, which is a continuation-in-part of Ser. No. 195,717, Feb. 14, 1994, abandoned, said Ser. No. 240,520, is a continuation of Ser. No. 953,251, Sep. 30, 1992, abandoned, said Ser. No. 221,013, said Ser. No. 220,999, said Ser. No. 197,604, said Ser. No. 196,855, said Ser. No. 195,717, each is a continuation-in-part of Ser. No.953,251.

[51] Int. Cl.$^6$ ....................................................... A61F 9/00
[52] U.S. Cl. .................................................. 606/107; 623/6
[58] Field of Search .................................... 606/107, 108; 623/6; 401/83, 84; 285/334

[56] References Cited

U.S. PATENT DOCUMENTS

| | | | |
|---|---|---|---|
| 2,495,342 | 1/1950 | Moore | 401/84 |
| 4,836,201 | 6/1989 | Patton et al. | 606/107 |
| 4,919,130 | 4/1990 | Stoy et al. | 606/107 |
| 4,934,363 | 6/1990 | Smith et al. | 606/107 |
| 4,955,889 | 9/1990 | Van Gent | 606/107 |
| 5,494,484 | 2/1996 | Feingold | 623/6 |
| 5,496,328 | 3/1996 | Nakajima et al. | 606/107 |

*Primary Examiner*—Robert A. Hafer
*Assistant Examiner*—Justine R. Yu
*Attorney, Agent, or Firm*—Klima & Pezzlo, P.C.

[57] ABSTRACT

A deformable intraocular lens insertion system comprising a lens injecting device and a lens cartridge with a rotary connecting arrangement between the lens injecting device and the lens cartridge. The invention includes preloading the deformable intraocular lens insertion system, in particularly the lens cartridge to reduce the amount of packaging, prevent damage to the deformable intraocular lens during packaging and shipping, allow the preloaded lens cartridge to be autoclaved as a unit, and eliminate the step of loading the lens cartridge with the deformable intraocular lens by the end user to prevent potential damage during this step.

15 Claims, 14 Drawing Sheets

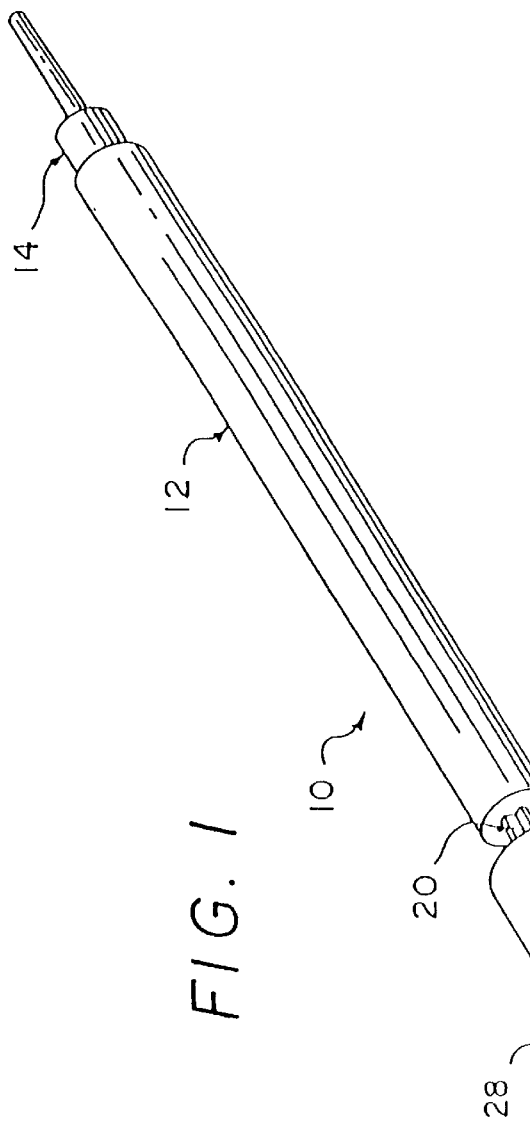
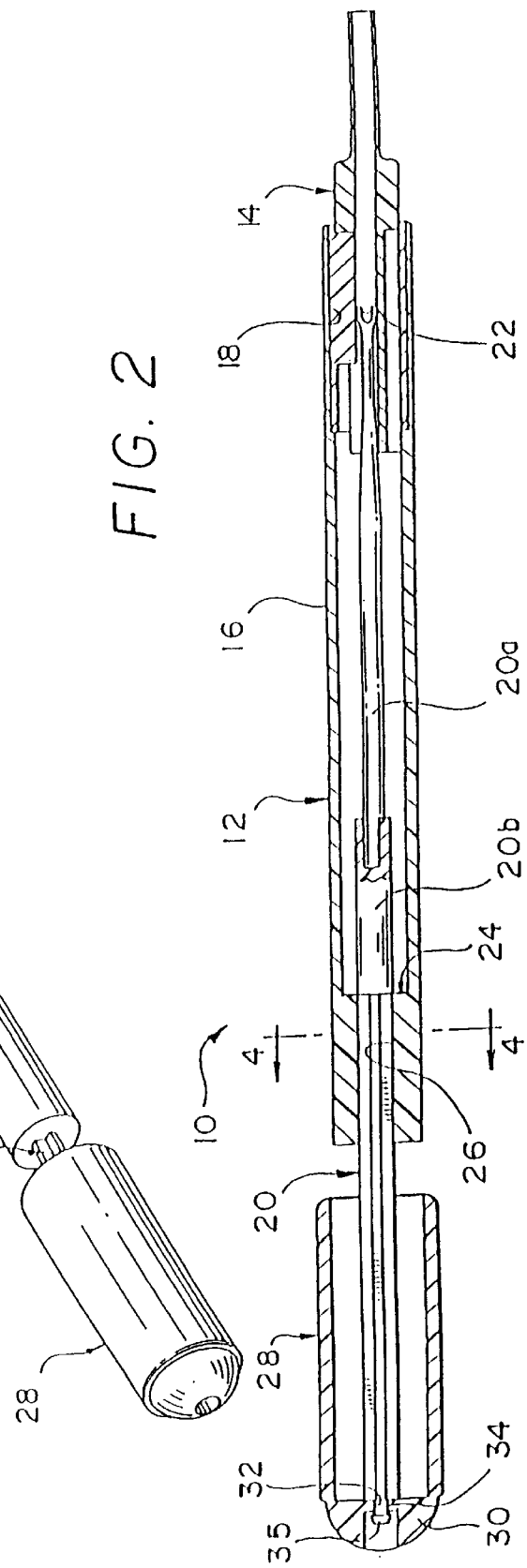

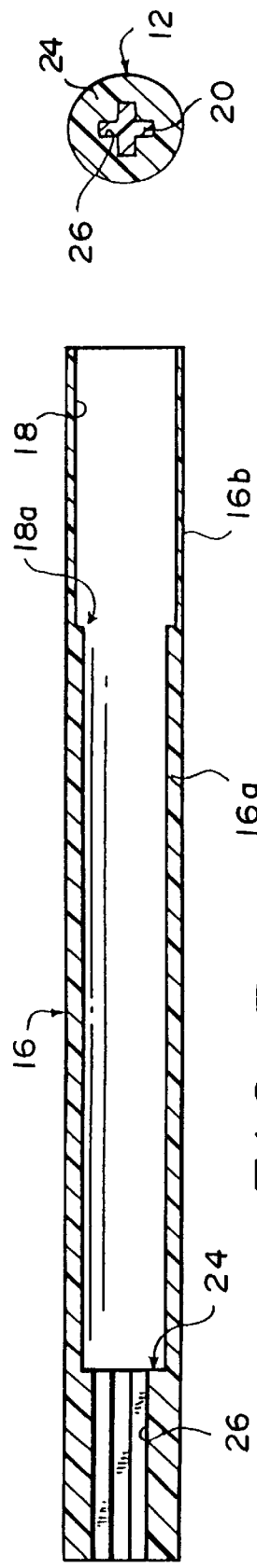
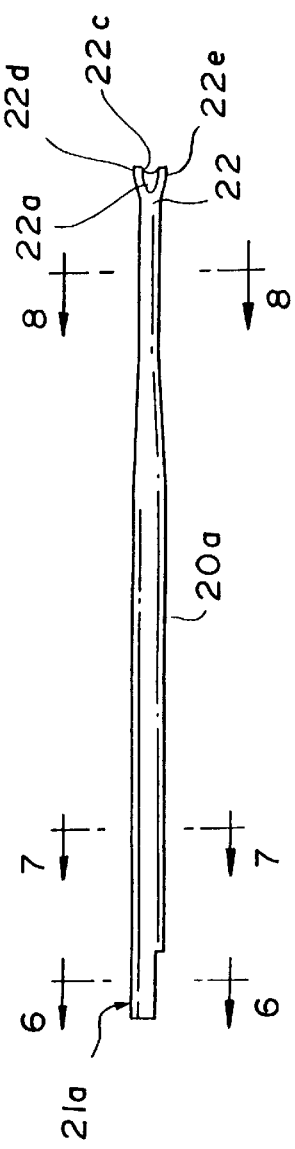
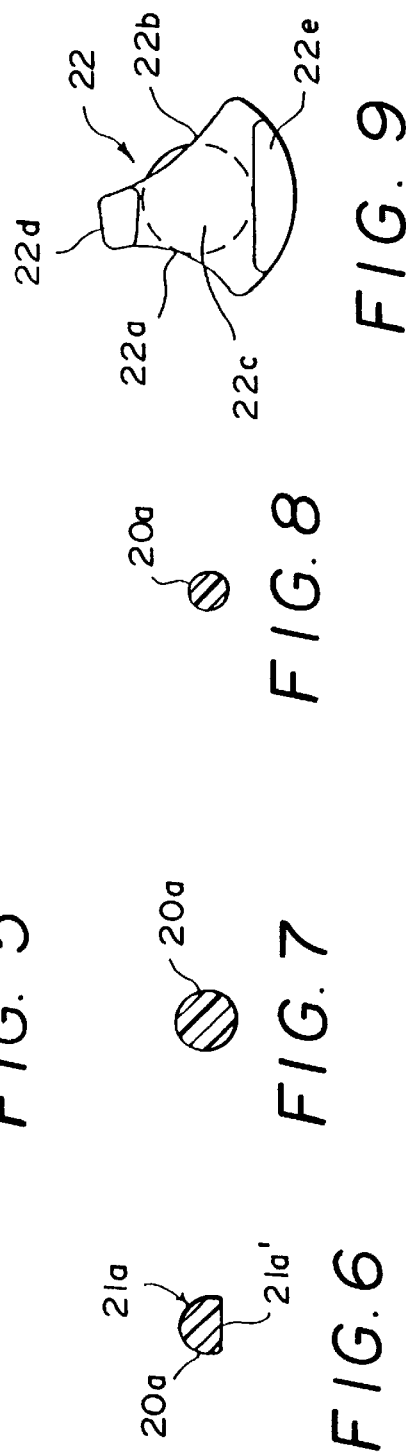
FIG. 3  FIG. 4  FIG. 5  FIG. 6  FIG. 7  FIG. 8  FIG. 9

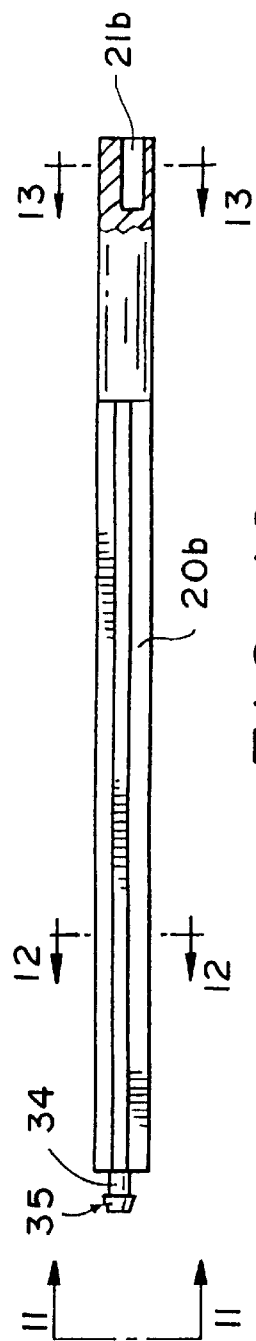
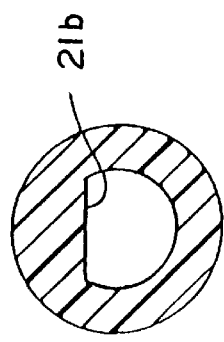
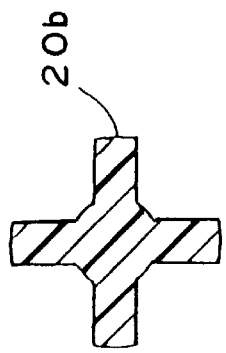
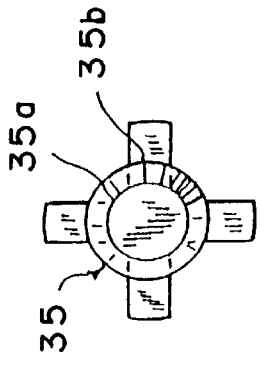
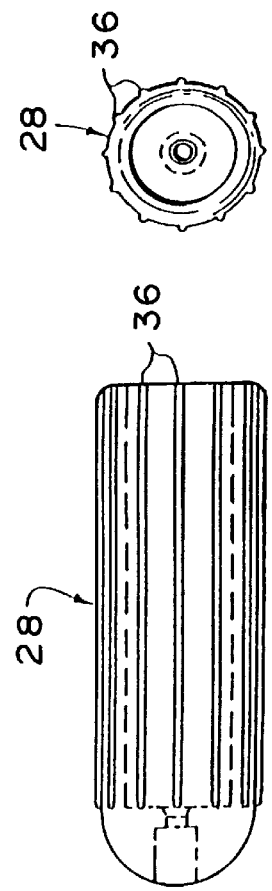
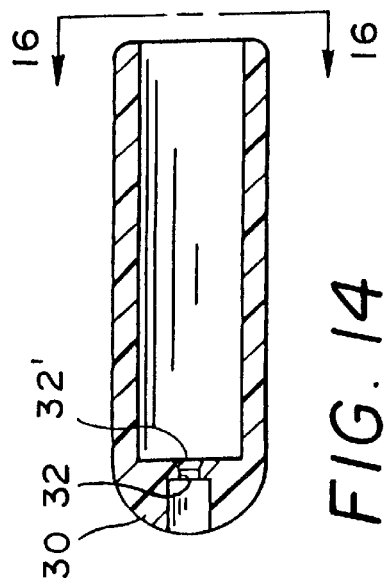

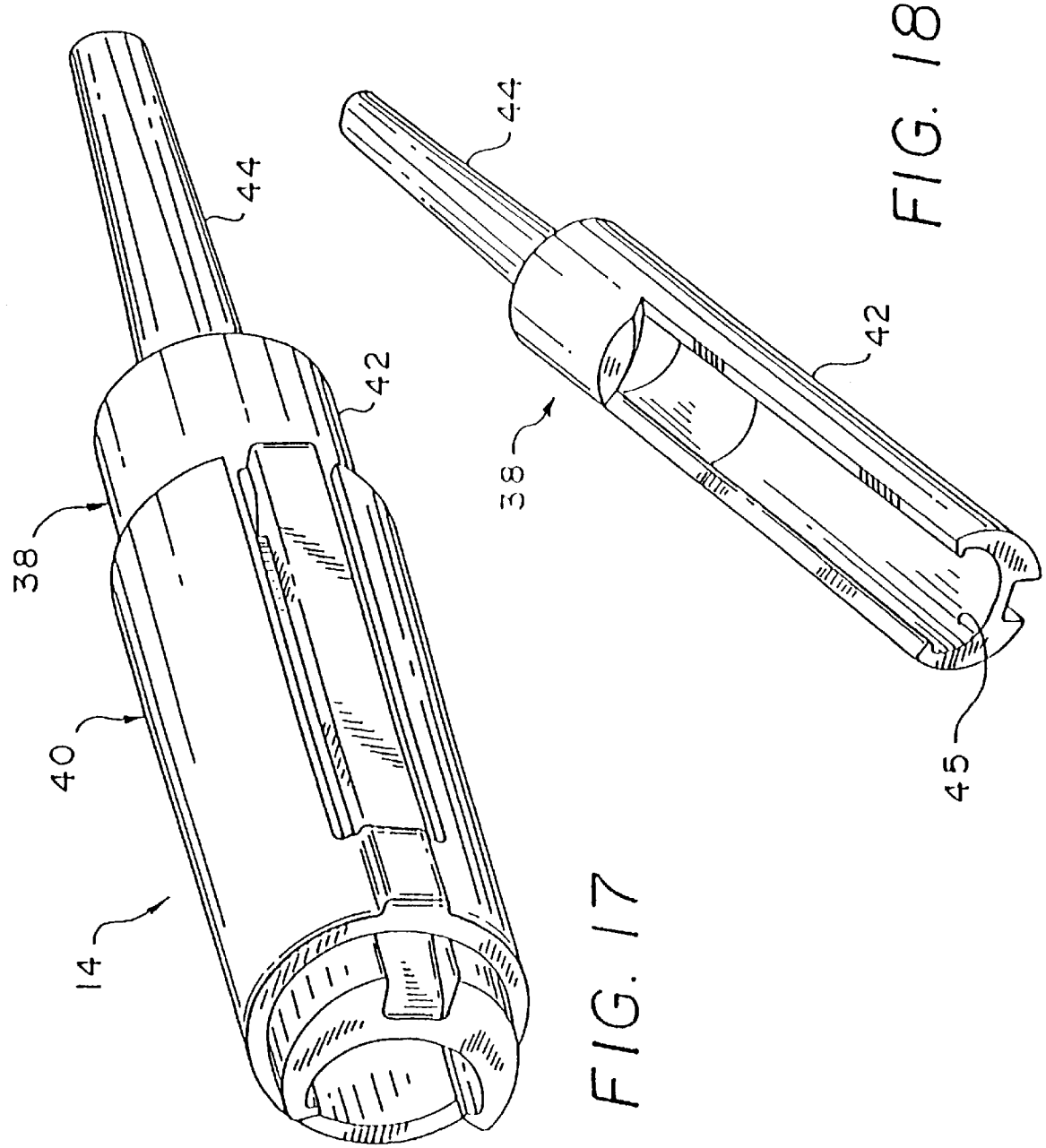

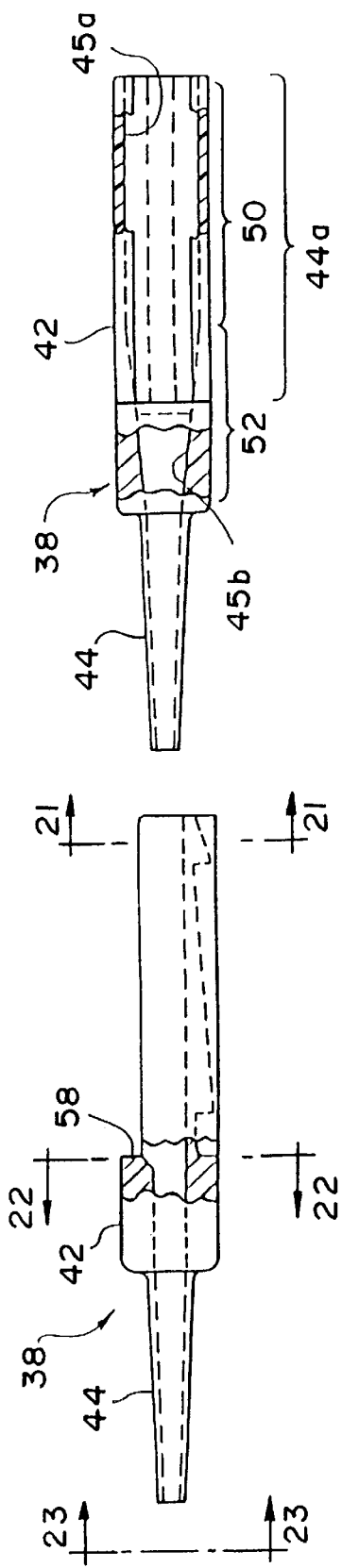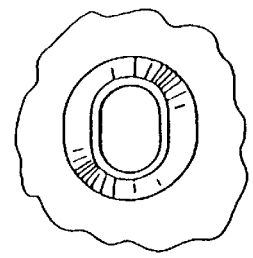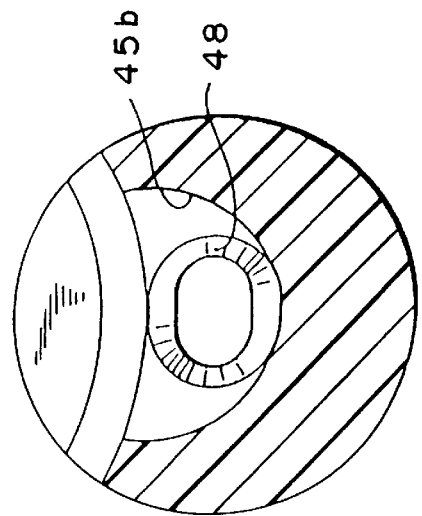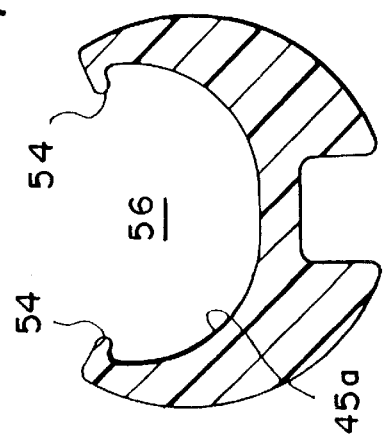
FIG. 20
FIG. 23
FIG. 19
FIG. 22
FIG. 21

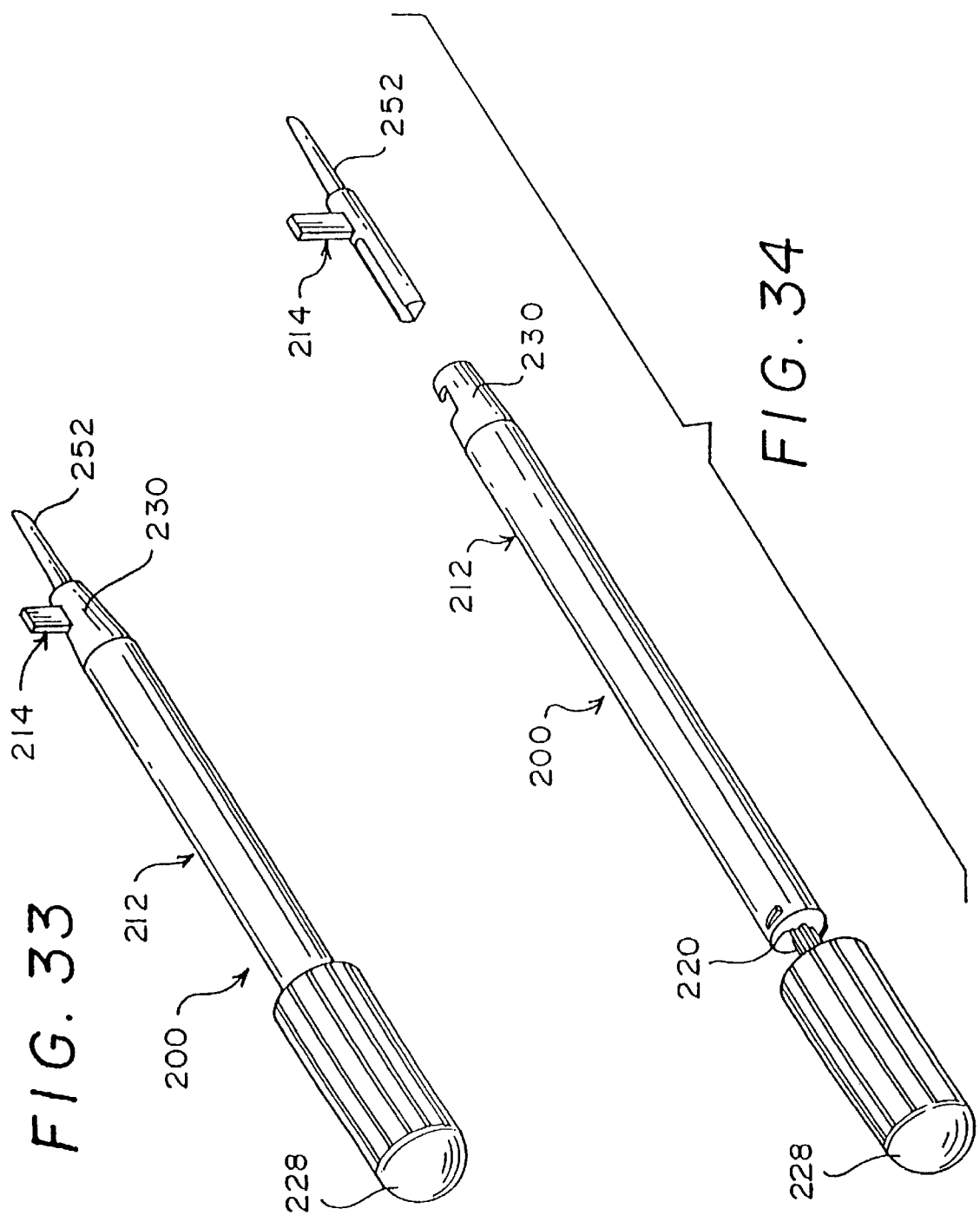

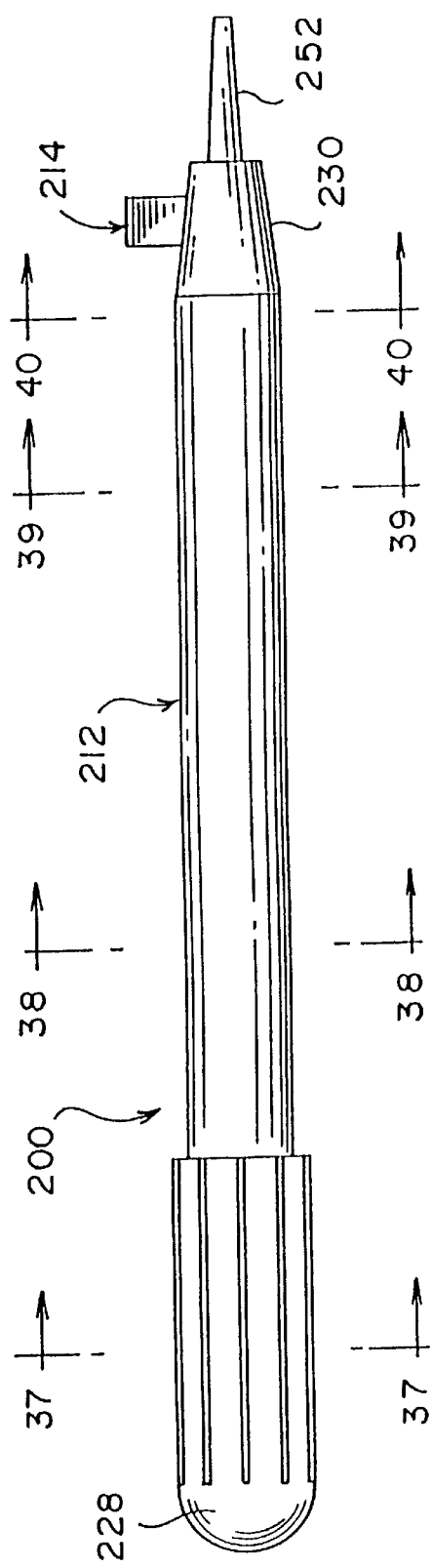
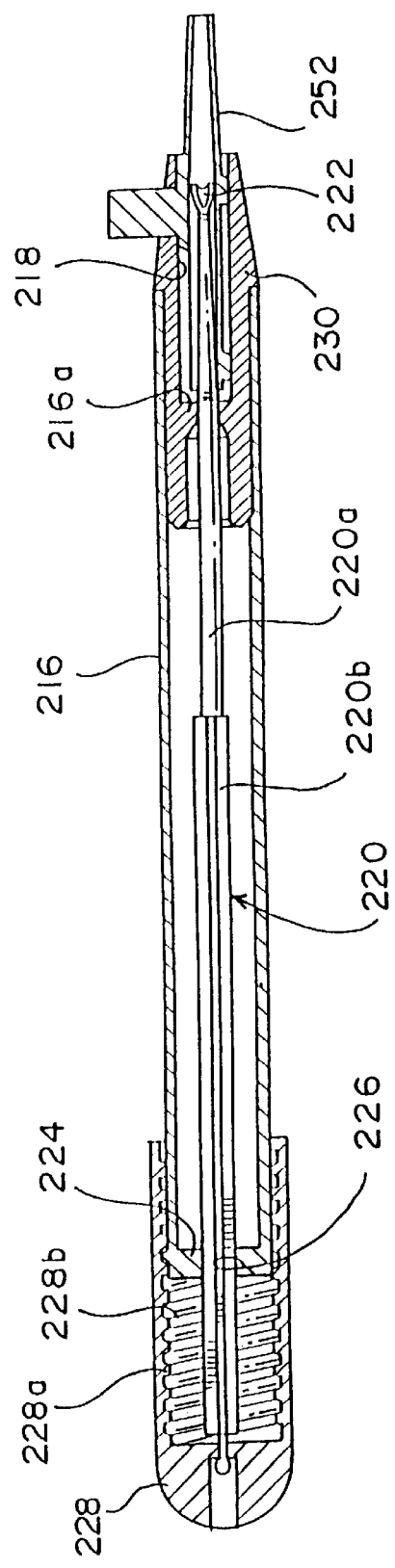
FIG. 35
FIG. 36

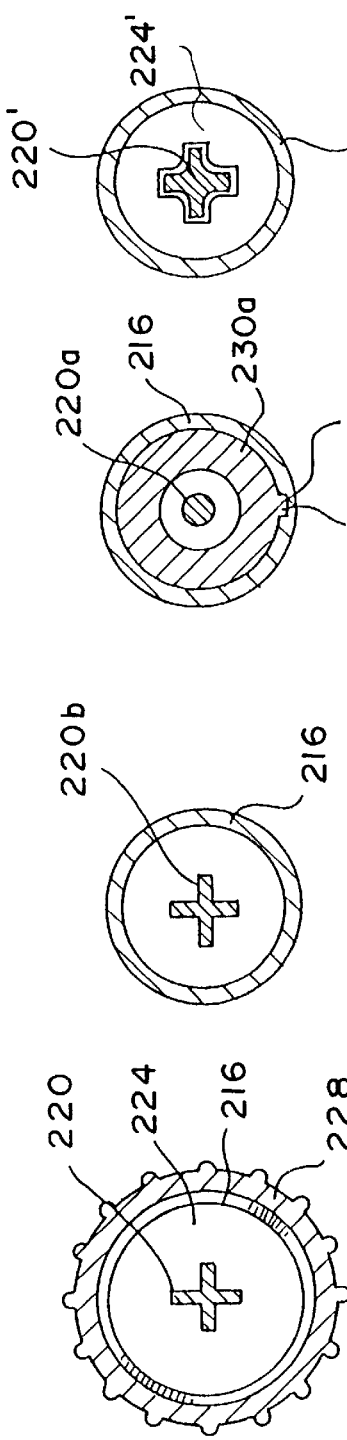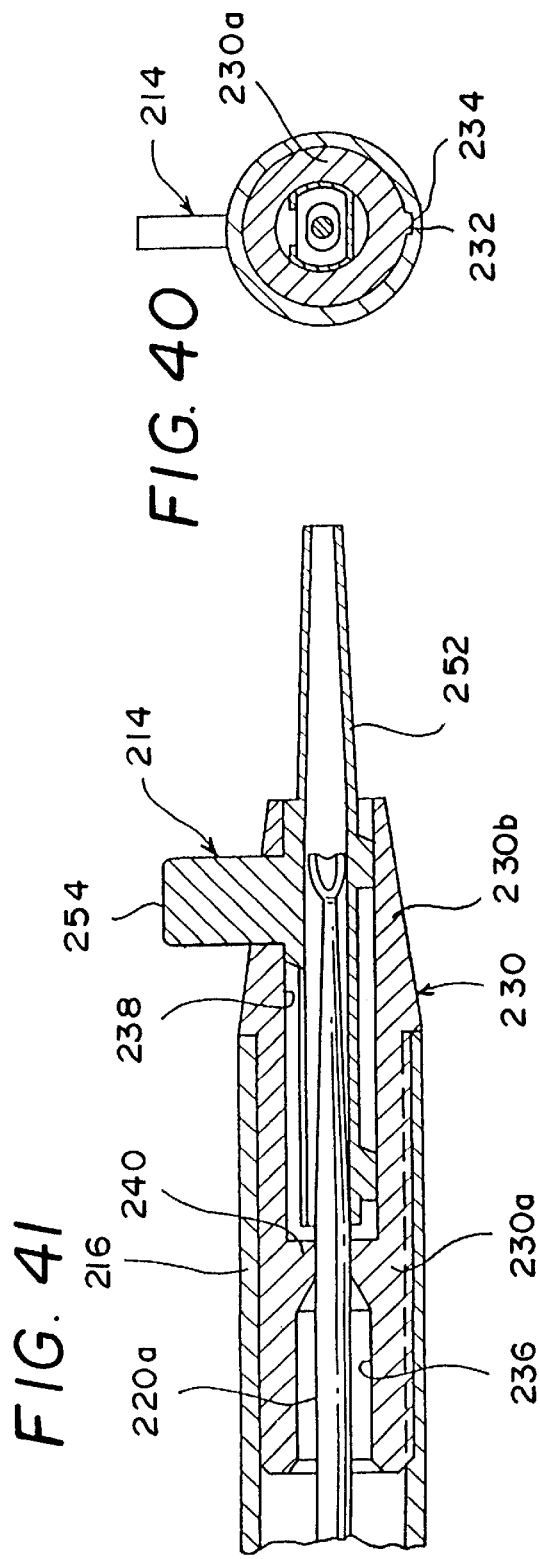

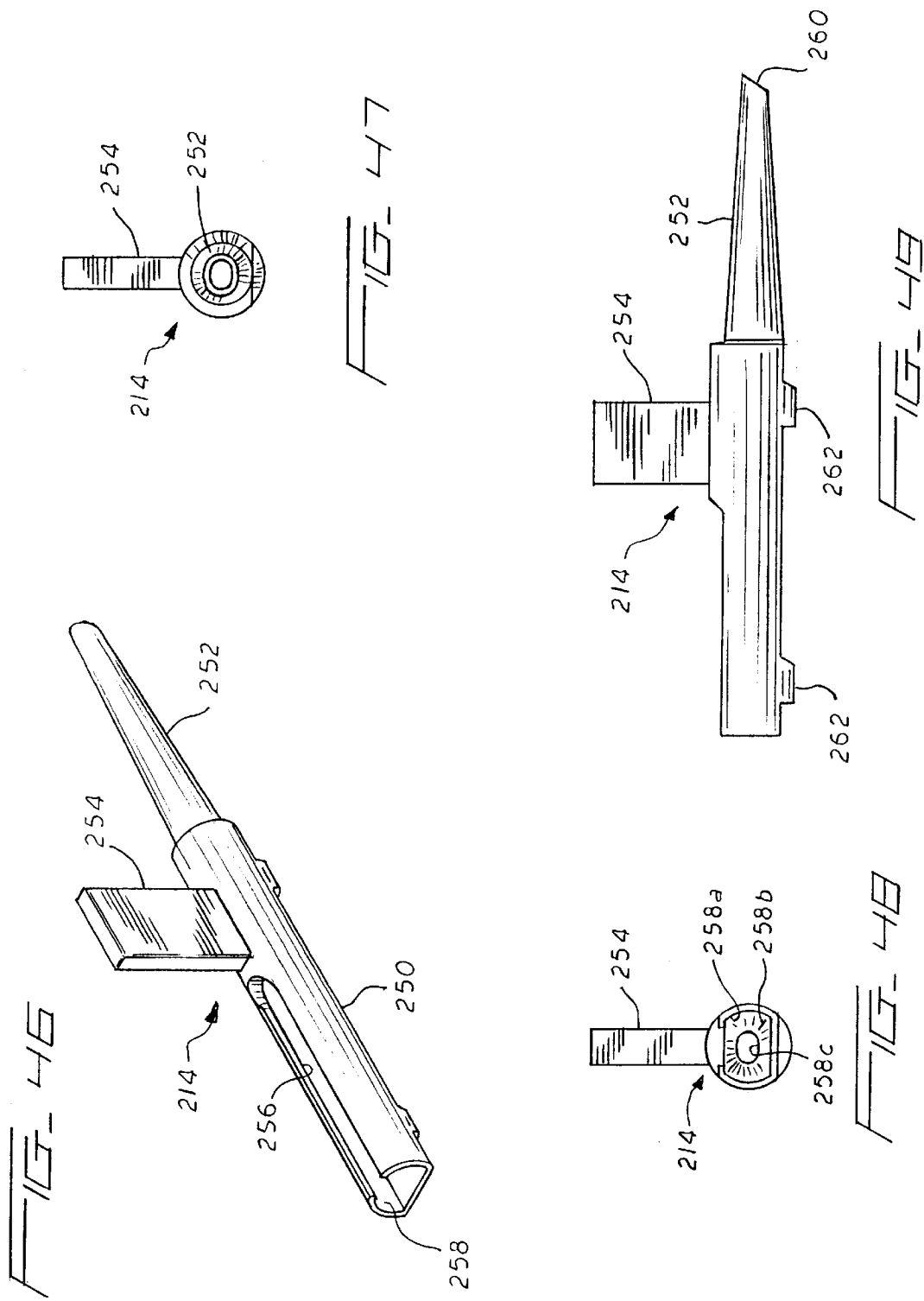

DEFORMABLE INTRAOCULAR LENS INSERTION SYSTEM

RELATED APPLICATION(S)

This is a continuation-in-part of U.S. patent application entitled "DISPOSABLE INTRAOCULAR LENS INSERTION SYSTEM", Ser. No. 08/345,360 filed Nov. 18, 1994, now abandoned, which is a continuation-in-part of:

(1) U.S. patent application entitled "INTRAOCULAR LENS INSERTION SYSTEM", Ser. No. 08/240,520 filed Jul. 19, 1994, now abandoned, (2) U.S. patent application entitled "DEFORMABLE INTRAOCULAR LENS INSERTION SYSTEM", Ser. No. 08/221,013 filed Apr. 1, 1994, now U.S. Pat. No. 5,494,484;

(3) U.S. patent application entitled "INTRAOCULAR LENS INJECTION SYSTEM", Ser. No. 08/220,999 filed on Apr. 1, 1994, now abandoned;

(4) U.S. patent application entitled "DEFORMABLE INTRAOCULAR LENS CARTRIDGE", Ser. No. 08/197,604 filed Feb. 17, 1994, now U.S. Pat. No. 5,499,987;

(5) U.S. patent application entitled "HINGELESS INTRAOCULAR LENS MICROCARTRIDGES, Ser. No. 08/196,855 filed on Feb. 15, 1994;

(6) U.S. patent application entitled "METHODS OF IMPLANTATION OF INTRAOCULAR LENSES", Ser. No. 08/195,717 filed on Feb. 14, 1994, now abandoned; and wherein (1) is a continuation and (2)–(6) are continuation-in-part applications of U.S. patent application entitled "INTRAOCULAR LENS INSERTION SYSTEM", Ser. No. 07/953,251 filed Sep. 30, 1992, now abandoned; and All of the above cited U.S. Patent Applications are fully incorporated by reference herein.

FIELD OF THE INVENTION

This invention relates to a deformable intraocular lens insertion system including a lens injecting device and a lens cartridge that can be connected and locked together after loading the deformable intraocular lens into the lens cartridge. Further, the present invention relates to a deformable intraocular lens insertion system having one or more disposable components, in particular a deformable intraocular lens insertion system comprising two separate main components including a disposable lens injecting device and a disposable lens cartridge.

BACKGROUND OF THE INVENTION

The deformable intraocular lens insertion system currently being sold and marketed by STAAR Surgical Company of California has gain widespread acceptance in the field of deformable intraocular lens implantation. The current system utilizes an injector made of titanium so that the unit can be autoclaved and reused numerous times. The components of the titanium injector are machined from bar stock to a high degree of accuracy according to current specifications, and then the components are assembled into the final injector unit. The cost of the materials, and labor costs involve with machining and assembly are substantial providing an incentive to seek less expensive alternatives. Further, the steps of cleaning and autoclaving the injector unit between operations is a time burden and nuisance to busy surgeon practitioners having back-to-back operation schedules. In addition, the injector must be properly autoclaved to ensure complete cleaning and sterilization to prevent spread of diseases causing eye infections or other infectious diseases, prevent transmission of body fluid and prevent resulting liability problems to surgeon practitioners. These and other considerations have led to the development of the present invention.

SUMMARY OF THE INVENTION

An object of the present invention is to provide an improved deformable intraocular lens insertion system.

A second object of the present invention is to provide a deformable intraocular lens insertion system comprising a lens injecting device and lens cartridge that can be connected and locked together.

A third object of the present invention is to provide a deformable intraocular lens insertion system including a lens injecting device and lens cartridge that can be connected together by a rotary connection therebetween.

A fourth object of the present invention is to provide a deformable intraocular lens insertion system comprising a lens injecting device and lens cartridge that can be connected and locked together by a rotary connection therebetween.

A fifth object of the present invention is to provide a deformable intraocular lens insertion system comprising one or more disposable components.

A sixth object of the present invention is to provide a fully disposable deformable intraocular lens insertion system comprising a disposable lens injecting device and a disposable lens cartridge.

A seventh object of the present invention is to provide a disposable lens injecting device for a deformable intraocular lens insertion system.

An eighth object of the present invention is to provide a disposable lens cartridge for a deformable intraocular lens insertion system.

A ninth object of the present invention is to provide a disposable lens cartridge having a downwardly tapering passageway for further folding the deformable intraocular lens as it moves through the lens cartridge.

A tenth object of the present invention is to provide a lens cartridge preloaded with a deformable intraocular lens.

An eleventh object of the present invention is to provide a deformable intraocular lens insertion system comprising a lens injecting device and a lens cartridge that can be connected and locked together by a bayonet-type connection therebetween.

A twelfth object of the present invention is to provide a deformable intraocular lens insertion system comprising a lens injecting device with a slot for accommodating a protrusion of the lens cartridge wherein the slot is configured to connect and lock the lens cartridge and a lens injecting device together.

A thirteenth object of the present invention is to provide a deformable intraocular lens insertion system comprising a lens injecting device with a longitudinal slot leading to a transverse slot for accommodating a protrusion of the lens cartridge for connecting and locking the lens cartridge and lens injecting device together.

A fourteenth object of the present invention is to provide a deformable intraocular lens insertion system having a pre-loaded deformable intraocular lens for storage and shipment.

A fifteenth object of the present invention is to provide an intraocular lens insertion system comprising a lens injecting device and lens cartridge with the deformable intraocular lens pre-loaded in the lens cartridge for storage and shipment.

These and other objects can be achieved by various embodiments of the present invention. Specifically, the present invention is directed to the main features of:

1) a rotary connection between the lens cartridge and the lens injecting device for connecting the lens cartridge to the lens injecting device;

2) a rotary connection between the lens cartridge and the lens injecting device for releasably connecting the lens cartridge to the lens injecting device to allow these components to be assembled and disassembled;

3) a rotary connection between the lens cartridge and the lens injecting device for permanently connecting the lens cartridge to the lens injecting device to prevent these components from being disassembled once assembled;

4) a rotary connection between the lens cartridge and the lens injecting device to both releasably connect and releasably lock the lens cartridge to the lens injecting device to allow these components to be assembled and disassembled, however, positively locking these components together to prevent inadvertent disassembly;

5) one or more components of the deformable intraocular lens insertion system are disposable. Preferably, the entire system excluding the deformable intraocular lens itself is disposable to provide the full advantages according to the present invention;

6) preloading the deformable intraocular lens insertion system with a deformable intraocular lens; and 7) preloading the lens cartridge with the deformable intraocular lens.

The rotary connection feature allows for quick and secure connection between the lens cartridge and the lens injecting device. It is important that when the lens cartridge is connected to the lens injecting device that there is no relative movement between the lens cartridge and lens injecting device, especially in the longitudinal and transverse directions of the lens injecting device to maintain the handling features of the apparatus during the surgical procedure. Any disassembly or looseness between the lens cartridge and lens injecting device can cause misalignment of the plunger tip with the deformable intraocular lens causing lens damage, or worse could cause potential damage to the eye.

The rotary connection can be provided by a large variety of designs that involve threads, locking tabs, interference fit or snap fit connection, and many other types of rotary mechanical connections. A preferred embodiment utilize a bayonet-type connection, which involves relative longitudinal movement followed by transverse movement between the lens cartridge and lens injecting device. One type of bayonet-type connection can be achieve by providing one end of the lens injecting device with a longitudinal slot leading to a transverse slot for cooperating with a tab or protrusion on the lens cartridge.

A preferred embodiment of the slot-type connection includes providing the transverse slot with means for positively gripping or locking the tab of the lens cartridge. For example, locking tabs, interference fit connection, snap fit connection can be provided between structure located at, in or adjacent to the transverse slot and the tab of the lens cartridge. A preferred embodiment is provided with a transverse slot having a first transverse slot portion dimensioned in width slightly less than the width of the tab of the lens holder providing some interference and resistance when the tab of the lens cartridge is rotated through the first transverse slot portion. The first transverse slot portion extends to a second transverse slot portion dimensioned in width slightly wider that the width of the first transverse slot portion. This arrangement provides a pair of opposed locking tabs in the transverse slot so that when the tab of the lens cartridge is rotated to the fully locked position, the tab snap fits into the second transverse slot portion preventing inadvertent disassembly of the lens cartridge from the lens injecting device. Specifically, the trailing edges of the tab of the lens holder become locked due to interference with the locking tabs in the transverse slot.

This arrangement can be designed to permanently connect the lens cartridge to the lens injecting device by designing the snap fit connection to engage so as to essentially permanently connect the components in such a manner that disassembly can only be obtained by destruction or damage to one or more of the components. However, this arrangement is particularly suitable to allow the components to be separated or damaged by designing the snap fit connect to engage in such a manner that allows disassembly when a certain level of force is applied without any significant damage or wear to the components.

The components of the deformable intraocular lens insertion system according to the present invention must withstand sterilization methods, in particular autoclaving, in order to be practically utilized. Preferably, the components of the intraocular lens insertion system according to the present invention are made from plastic, most preferably autoclavable plastic (i.e. plastic having a melting point above approximately 121 degree Celsius) such as polysulfone, polycarbonate, nylon-66, TEFLON and KYNAR that can withstand the conditions of high temperature and pressure inside conventional autoclaving units. Further, the use of plastic allows the components of the deformable intraocular insertion system to be injection molded and quickly assembled significantly reducing cost in the construction thereof verses a titanium or stainless steel injector.

An embodiment of the disposable insertion system comprises two separate main components including a lens injecting device and a lens cartridge. The lens injecting device includes a barrel with a lens cartridge receiver for accommodating the lens cartridge, which accommodates a folded deformable intraocular lens. The lens injecting device preferably includes a cylindrical barrel having the lens cartridge receiver positioned at one end, and a movable plunger accessible at an opposite end. Specifically, the end fitted with the movable plunger is provided with a guide for defining a passageway for accommodating the movable plunger. The guide is preferably molded as part of the inside of the cylindrical barrel, however, alternatively can be made as a separate piece and then assembled in some suitable manner inside the cylindrical barrel.

The guide preferably is configured to allow sliding movement of the movable plunger in a longitudinal direction with relation to the cylindrical barrel, however, not allowing rotational movement of the movable plunger with respect to the cylindrical barrel. For example, the guide is provided with a keyway preventing relative rotation. In one preferred embodiment, the passageway through the guide has a passageway with a cross-sectional shape matching a movable plunger preventing relative rotation.

The lens cartridge receiver located at one end of the cylindrical barrel in preferably a cylindrical shaped receiver for accommodating the lens cartridge containing the deformable intraocular lens. Further, the cylindrical barrel is provided with means for defining the rotary connection for connecting and securely retaining the lens cartridge inside the front open end of the cylindrical barrel. In addition to the rotary connection, an interference type connection can be provided between the open front end of the cylindrical barrel and the lens cartridge so that these components are securely connected together when inserting the lens cartridge into the open end of the cylindrical barrel. The interference connection can be provided by sizing a portion of or the entire outer dimension of the lens cartridge slightly greater than the inner dimension of the open end of the lens cartridge receiver. Further, one or both components can have tapering outer surfaces or locking tabs that interfere with each other to provide an interference or snap fit type connection.

One end of the plunger is provided with a manipulating tip for making contact with the deformable intraocular lens, forcing the deformable intraocular lens from the lens cartridge, and manipulating the deformable intraocular lens inside the eye. An opposite end of the plunger is provided with means for actuating the plunger. The opposite end can be provided with a freely rotating finger tip gripping device to allow a user to exert sufficient pressure on the end of the plunger to controllably force the deformable intraocular lens from the lens cartridge. For example, the finger tip gripping device is provided with a fluted exterior surface to facilitate gripping thereof, and a through hole having a predetermined size. The end of the plunger component is provided with an extension having a cylindrical tab end that can be forced into and through the through hole in the finger tip gripping device providing a snap connection between these components, and also allowing free rotation between these components.

The manipulating end is faceted in a particular manner to prevent damage to the deformable intraocular lens, particularly the trailing haptic, during the step of forcibly pushing the deformable intraocular lens through the nozzle of the lens cartridge and into the eye.

The present invention includes the concept of pre-loading the deformable intraocular lens in the deformable insertion system. Specifically, a potentially preferred method of making and selling deformable intraocular lens is to pre-load the deformable intraocular lens in the lens injecting device for purposes of storage and shipping. For example, the deformable intraocular lens can be manufactured, and then placed inside the lens injecting device or lens cartridge (i.e. inside deformable intraocular lens insertion system) prior to being packaged and shipped to a customer. This method reduces the amount of packaging by not requiring separate packages for the deformable intraocular lens and the lens cartridge and/or lens injecting device. Further, the lens cartridge and/or lens injecting device protects the deformable intraocular lens during the process of packaging, shipping and other handling, and eliminates the step of loading the deformable intraocular lens into the lens cartridge and/or lens injecting device by the surgeon that could potentially cause damage thereto. Further, pre-loading the lens can eliminate misuse during surgery.

This method would allow the lens cartridge and/or lens injecting device and pre-loaded deformable intraocular lens to be autoclaved together prior to insertion of the deformable intraocular lens.

BRIEF DESCRIPTION OF THE DRAWINGS

FIG. 1 is a perspective view of a preferred embodiment of the deformable intraocular lens insertion system according to the present invention.

FIG. 2 is a side longitudinal cross-sectional view of the deformable intraocular lens insertion system shown in FIG. 1.

FIG. 3 is a longitudinal side cross-sectional view of the cylindrical barrel of the deformable intraocular lens insertion system shown in FIG. 2.

FIG. 4 is a transverse cross-sectional view through the movable plunger, guide, and cylindrical barrel, as indicated in FIG. 2, to illustrating the movable plunger guiding arrangement.

FIG. 5 is a longitudinal side elevational view of the plunger portion having the manipulating tip.

FIG. 6 is a transverse cross-sectional view of the plunger portion, as indicated in FIG. 5.

FIG. 7 is a transverse cross-sectional view of the plunger portion, as indicated in FIG. 5.

FIG. 8 is a transverse cross-sectional view of the plunger portion, as indicated in FIG. 5.

FIG. 9 is an end elevation view of the manipulating tip of the plunger portion shown in FIG. 5.

FIG. 10 is a longitudinal side elevational view of the plunger portion that connects to the plunger portion shown in FIG. 5.

FIG. 11 is an end elevational view of the plunger portion shown in FIG. 10.

FIG. 12 is a transverse cross-sectional view of the plunger portion, as indicated in FIG. 10.

FIG. 13 is a transverse cross-sectional view of the plunger portion, as indicated in FIG. 11.

FIG. 14 is a cross-sectional view of the threaded gripping device to be connected to the plunger, as shown in FIG. 2.

FIG. 15 is a side elevational view of the threaded gripping device shown in FIG. 14

FIG. 16 is an end elevational view of the threaded gripping device shown in FIG. 14.

FIG. 17 is a perspective view of a preferred lens cartridge assembly according to the present invention.

FIG. 18 is a perspective view of the lens holding portion of the preferred lens cartridge assembly shown in FIG. 17.

FIG. 19 is a is a longitudinal side elevational view of the lens holding portion shown in FIG. 18.

FIG. 20 is a top planar view of the lens holding portion shown in FIG. 18.

FIG. 21 is a transverse cross-sectional view of the of the lens holding portion, as indicated in FIG. 19.

FIG. 22 is a transverse cross-sectional view of the lens holding portion, as indicated in FIG. 19.

FIG. 23 is an end elevational view of the end of the lens holding portion as indicated in FIG. 19.

FIG. 33 is a perspective view of another preferred embodiment of the deformable intraocular lens insertion system with the lens cartridge loaded in the device.

FIG. 34 is a broken away perspective view of the deformable intraocular lens insertion system with the lens cartridge removed from the device.

FIG. 35 is a longitudinal side elevational view of the deformable intraocular lens insertion system shown in FIG. 33.

FIG. 36 is a longitudinal side cross-sectional view of the deformable intraocular lens insertion system shown in FIG. 35.

FIG. 37 is a transverse cross-sectional view of the deformable intraocular lens insertion system, as indicated in FIG. 35.

FIG. 37A is a transverse cross-sectional view of another deformable intraocular lens insertion system showing the matching cross-sectional shapes of the movable plunger and plunger guide having a configuration that allows only a one-way orientation there between.

FIG. 38 is a transverse cross-sectional view of the deformable intraocular lens insertion system, as indicated in FIG. 35.

FIG. 39 is a transverse cross-sectional view of the deformable intraocular lens insertion system, as indicated in FIG. 35.

FIG. 40 is a transverse cross-sectional view of the deformable intraocular lens insertion system is indicated in FIG. 35.

FIG. 41 is an exploded partial longitudinal side cross-sectional view of the deformable intraocular insertion system, as shown in FIG. 36.

FIG. 46 is a perspective view of a lens cartridge for use with the lens injecting device shown in FIGS. 33 and 34.

FIG. 47 is an end elevational view of the lens cartridge, as shown in FIG. 46.

FIG. 48 is a rear end elevational view of the lens cartridge, as shown in FIG. 46.

FIG. 49 is a side elevational view of the lens cartridge, as shown in FIG. 46.

DETAILED DESCRIPTION OF PREFERRED EMBODIMENTS

Figure 25:
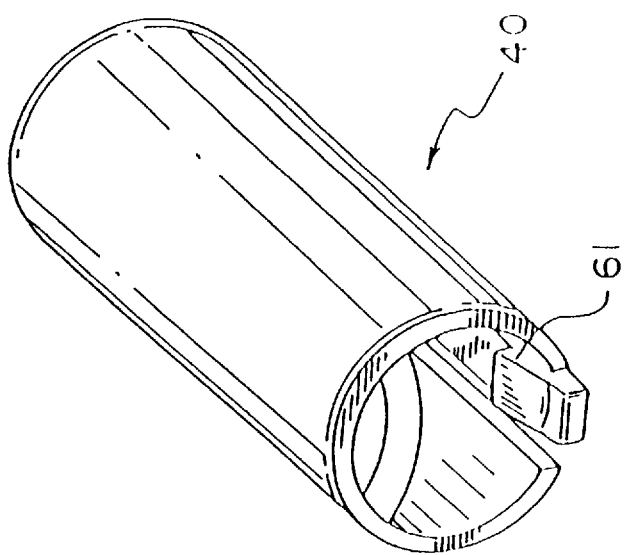
FIG. 25 is another perspective view of the sleeve portion of the preferred lens cartridge shown in FIG. 17.

The term deformable intraocular lens insertion system according to the present invention is used to define two separate main components including a lens injecting device and a lens cartridge. The lens injecting device includes a lens cartridge receiver for accommodating the lens cartridge, and the lens cartridge is configured to accommodate a deformable ("foldable") intraocular lens. The deformable intraocular lens is first loaded into the lens cartridge, and then the lens cartridge is loaded into the lens injecting device providing a deformable intraocular lens insertion system readied for conducting the implantation operation.

The term disposable in the context of the present invention is used to indicate that the one or more components of the deformable intraocular lens insertion system according to the present invention can be readily discarded after use due to the inexpensive nature of the design, construction, and materials of the components. The use of disposable components provides a variety of convenience factors such as preloading disposable lens cartridges with deformable intraocular lenses, improved handling characteristics, reducing weight of the lens injecting device, and most importantly ensuring a high level of sterility protecting the patient from disease and risk of complications.

A preferred embodiment of the deformable intraocular lens insertion system 10 according to the present invention is shown in FIG. 1. The intraocular lens insertion system 10 comprises two main components including a lens injecting device 12 and a lens cartridge assembly 14.

The lens injecting device 12 comprises a cylindrical barrel 16 having a lens cartridge receiver 18 located at one end thereof, as shown in FIG. 2. The cylindrical barrel 16 can have other suitable cross-sectional shapes, however, a cylindrical-shaped barrel is particular suitable for making, assembling, and utilizing the lens injecting device 12. The lens cartridge receiver 18 accommodates the lens cartridge assembly 14, which is securely connected to the lens injecting device 12 when inserted into the lens cartridge receiver 18. For example, an interference type connection can be provided between the lens injecting device 12 and the lens cartridge assembly 14 by making one or more outer dimensions of the lens cartridge assembly 14 slightly larger than one or more inner dimensions of the lens cartridge receiver 18. Alternatively or in addition, a snap type connection can be provided between the lens injecting device 12 and the lens cartridge assembly 14. Further, either or both type of connections can be made so that the lens cartridge is either removable or non-removable after insertion into the lens cartridge receiver 18. Preferably, the lens injecting device 12 and the lens cartridge assembly 14 are designed so that the lens cartridge assembly 14 can not be rotated within the lens cartridge receiver 18 to prevent any relative movement therebetween which can detract from the manipulating characteristics of the deformable intraocular lens insertion system.

The design of the cylindrical barrel 16 itself is shown in FIG. 3. The cylindrical barrel 16 comprises a barrel portion 16a having thicker walls to provide structural strength against bending in the longitudinal direction, and a barrel portion 16b having thinner walls defining the lens cartridge receiver 18. An inner edge 18a at the transition between the barrel portions 16a and 16b defines a stop for the lens cartridge assembly 14 when inserted into the lens cartridge receiver 18.

The lens injecting device 12 further includes a movable plunger 20 disposed within the cylindrical barrel 16. Specifically, the movable plunger 20 is movably disposed within the cylindrical barrel for movement forward or backwards with respect to the longitudinal direction of the cylindrical barrel 16. In the deformable intraocular lens insertion system 10, the movable plunger 20 comprises two movable plunger portions 20a and 20b, as shown in FIGS. 2, 5 and 10. The movable plunger portion 20a includes a manipulating tip 22 for engaging with the deformable intraocular lens for forcing the deformable intraocular lens from the loaded lens cartridge assembly 14. The two movable plunger portions 20a and 20b can have a one-piece construction, or can be made as two separate pieces connected together is some suitable manner.

The detailed design of the movable plunger portion 20a of the movable plunger 20 is shown in FIGS. 5 to 9, and the detailed design of the movable plunger portion 20b of the movable plunger 20 is shown in FIGS. 10 to 13.

The movable plunger portion 20a includes a connector portion 21a (FIG. 5) for connecting with a connector portion 21b (FIG. 10) of the movable plunger portion 20b. Preferably, an interference type connection and/or snap fit type connection is provided by the connector portions 21a and 21b to facilitate assembly. In the embodiment shown, a keyway type connection is provided by the flat surface 21a' of the connector portion 21a (FIG. 6) cooperating with the flat key surface 21b' of the connector portion 21b (FIG. 13). The keyway type connection prevents relative rotation between the movable plunger portions 20a and 20b after the movable plunger 20 is assembled.

The detail design of the manipulating tip 22 is shown in FIG. 9. The manipulating tip 22 is defined by a plurality of facets for manipulating the deformable intraocular lens from the lens cartridge and in the eye. Specifically, the manipulating tip comprises a curved surface facet 22a, curved surface facet 22b, concave surface facet 22c (FIG. 5), upper protrusion facet 22d, and lower protrusion facet 22e.

In the preferred embodiment of the deformable intraocular lens insertion system 10, the movable plunger 20 is slidably disposed within the cylindrical barrel 16. Specifically, a plunger guide 24 is disposed within the cylindrical barrel 16, which plunger guide 24 is provided with a passageway 26 for slidably supporting the movable plunger 20. In the embodiment shown, the inner dimensions of the passageway 26 of the plunger guide 24 are slightly greater than the outer dimensions of the movable plunger 20 to provide the guide arrangement. Further, the cross-section shape of the passageway 26 is preferably made the same as the cross-sectional shape of the movable plunger 20 (i.e. matching shapes) to enhance a close tolerance fit therebetween to improve sliding accuracy. More preferably, the cross-sectional shapes of the passageway 26 of the plunger guide 24 and the movable plunger 20 are interlocking to prevent relative rotation between the cylindrical barrel 16 fixed to the plunger guide 24 and the movable plunger 20, again to enhance the manipulating characteristics of the deformable intraocular lens insertion system 10. For example, the cross-sectional shapes of the passageway 26 of the plunger guide 24 and the movable plunger 20 can be cross-shaped to provide an interlocking arrangement, as shown in FIG. 4.

In the embodiment shown in FIG. 2, the plunger guide 24 is part of the cylindrical barrel 16. For example, the cylindrical barrel 16 can be injection molded from plastic to include the plunger guide 24 as a one-piece unit. Alternatively, the plunger guide 24 can be made as a separate piece, and then assembled inside the cylindrical barrel 16. Further, in the embodiment shown, the plunger guide 24 is provided at one end of the cylindrical barrel 16, however, the plunger guide 24 can be located at a position inside the cylindrical barrel 16 away from the end of the cylindrical barrel 16.

The movable plunger 20 is provided with a finger tip gripping device 28 located at an end opposite to the manipulating tip 22. The gripping device 28 is preferably connected in a freely rotating manner with the end of the movable plunger 20, however, a non-rotating type connection can also be utilized.

In the preferred embodiment of the deformable intraocular insertion system 10, the gripping device 28 is essentially cylindrical-shaped, and has an inner diameter slightly greater than the outer diameter of the cylindrical barrel 16 to allow an end portion of the cylindrical barrel 16 to be accommodated inside the gripping device 28 when the movable plunger 20 is moved towards the right in FIG. 1. The outer surface of the gripping device can be fluted to increasing the gripping ability by a user's finger tips.

The gripping device 28 is provided with an end portion 30 having a passageway 32 for accommodating a protrusion 34 having a cylindrical tab 35 of the movable plunger 20. Specifically, the cylindrical tab 34 is provided with a conical tapering surface 35a having a lip 35b (FIG. 11) with a slightly greater diameter than the passageway 32 in the end portion 30 to provide a snap fit connection therebetween. Thus, the gripping device 28 can be easily assembled onto the movable plunger 20 by forcing the cylindrical tab through the passageway 32.

The detailed design of the gripping device 28 is shown in FIGS. 14 to 16. In FIG. 14, the passageway 32 in the end portion 30 of the gripping device 28 is provided with a conical tapering surface 32' to facilitate entry of the hooked end 35 of the movable plunger 20 into and through the passageway 32 during assembly. The outside of the gripping device 28 can be provided with a plurality of longitudinal ribs 36 equally spaced around the perimeter of the gripping device 28, as shown in FIGS. 15 and 16.

A preferred embodiment of the lens cartridge assembly 14 is shown in FIGS. 17 to 28. The lens cartridge assembly 14 comprises two main separate components including a lens cartridge 38 and a sleeve portion 40. The lens cartridge 38 is defined by a body portion 42 having a passageway 45, and a nozzle portion 44 having a passageway 48, as shown in FIGS. 18 to 22.

The body portion 42 is defined by a lens receiving portion 50 and a lens transitioning portion 52, as shown in FIG. 20. The lens receiving portion 50 has a fixed cross-sectional size and shaped passageway 45a (FIGS. 20 and 21). Specifically, the lens receiving portion 50 has a C-shaped cross section passageway that does not vary in shape or size along the length of the lens receiving portion 50. Further, the lens transitioning portion 52 has a variable or downwardly tapering cross-sectional size passageway. The passageway through the body portion includes an open passageway 45a of length 44a and a closed passageway 45b (FIGS. 20 and 22).

Specifically, the transitioning portion 52 has a C-shaped cross section defining the beginning of closed passageway 45b, which matches the transverse shape of passageway 45a, however, the shape changes from C-shaped (i.e. open passageway design), to D-shaped (i.e. closed passageway design), to oval (i.e. closed passageway design) along the length of the lens transitioning portion 52.

The lens receiving portion 50 and an initial portion of the lens transitioning portion 52 having a C-shaped cross section passageway include a pair of gripping edge protrusions 54 positioned on either side of opening 56 into passageway 45a. The gripping edge protrusions 54 confine the outer edges of the folded deformable intraocular lens once inserted into the lens receiving portion 50.

The nozzle portion 44 is located at one end of the body portion 42. Preferably, the lens cartridge 38 including the body portion 42 and nozzle portion 44 are a molded one-piece construction.

The nozzle portion 44 having passageway 48 has an oval-shaped cross-sectional shape. However, the cross-sectional size tapers downwardly from the body portion 42 to the end of the nozzle portion 44 (See tapering passageway 48 in FIG. 22).

The detailed design of the sleeve portion 40 is shown in FIGS. 24 to 29. The sleeve portion 40 is essentially cylinder-shaped. Specifically, the inner diameter of the sleeve portion 40 is approximately equal to the outer diameter of the cylindrical body portion 42 of the lens cartridge 38. The lens cartridge assembly 14 is assembled by inserting the body portion 42 of the lens cartridge 38 into the sleeve portion 40 until the end of the sleeve portion 40 contacts with the edge 58 (FIG. 19) of the lens cartridge 38.

Figure 25A:
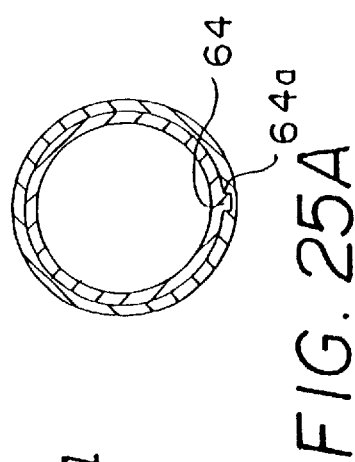
FIG. 25A is a transverse cross-sectional view showing the protrusion the lens cartridge assembly cooperating with the slot in the lens cartridge receiver to prevent relative rotation therebetween.
Figure 24:
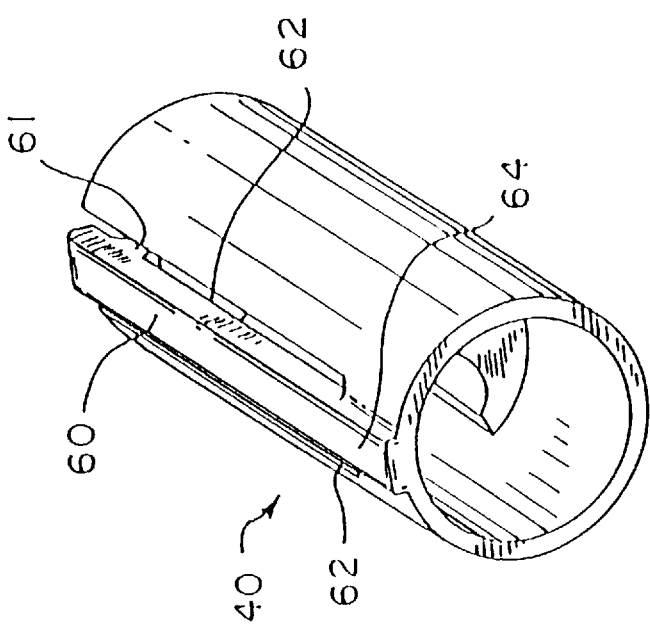
FIG. 24 is a perspective view of the sleeve portion of the preferred lens cartridge assembly shown in FIG. 17.
Figure 27:
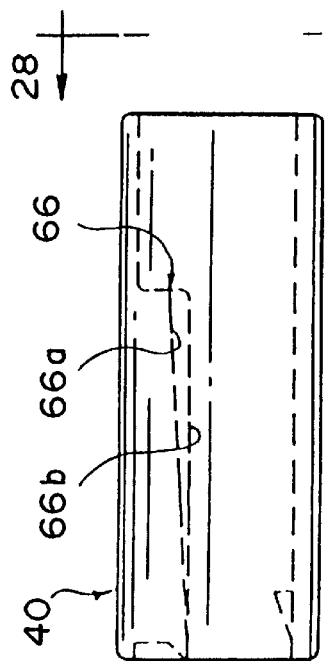
FIG. 27 is longitudinal side elevational view of the sleeve portion shown in FIG. 24 with ghost images of the guiding surfaces of the protrusion located inside the sleeve portion.
Figure 29:
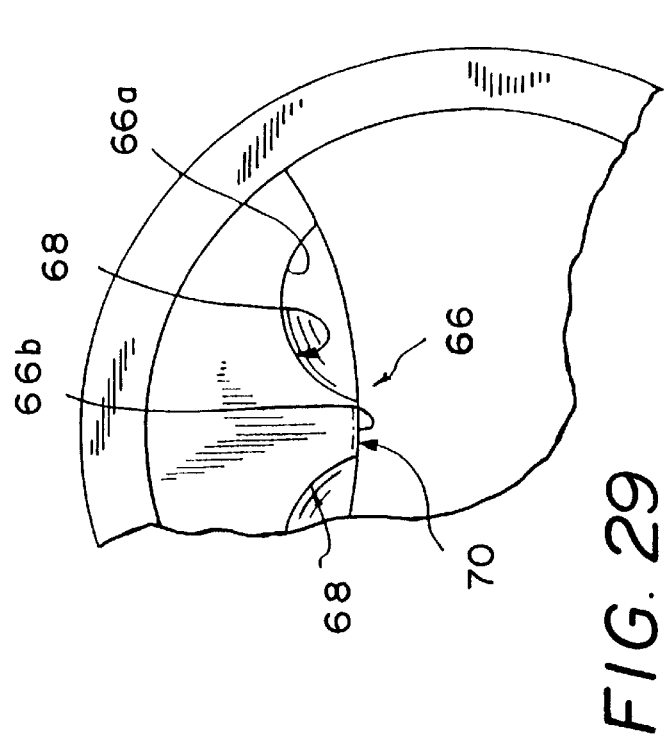
FIG. 29 is an exploded partial end elevational view of the sleeve portion shown in FIG. 27.
Figure 26:
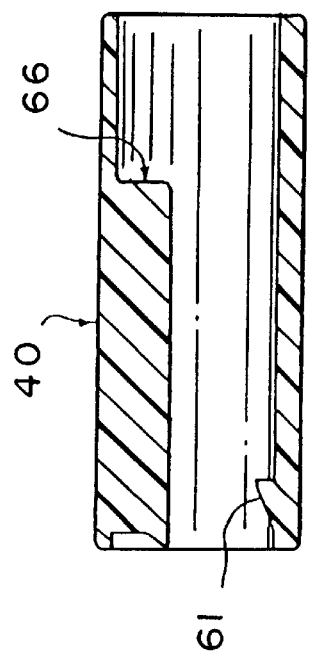
FIG. 26 is a longitudinal cross-sectional view of the sleeve portion shown in FIG. 24.
Figure 28:
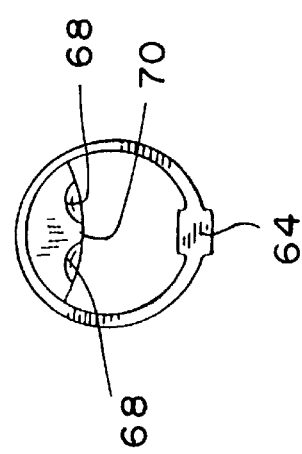
FIG. 28 is an end elevational view of the of the sleeve portion, as indicated in FIG. 27.

The sleeve portion 40 includes a cantilever spring 60 having a catch 61 provided at the end thereof. The cantilever spring 60 is formed by providing a pair of parallel slits 62 in the wall of the sleeve portion 40. Further, the cantilever spring 60 is thicker than the wall of the sleeve portion 40 and extends along a portion of the outside thereof defining a protrusion 64 cooperating with a groove 64a in the lens cartridge receiver 18, as shown in FIG. 25A, defining a keyway arrangement to prevent the lens cartridge assembly 14 from rotating inside the lens injecting device 12.

The sleeve portion 40 is provided with a lens guiding protrusion 66 extending from the inner surface thereof into an upper portion of the passageway 45 in the body portion 42. The lens guiding protrusion 66 is defined by a pair of downwardly tapering grooves 68, 68 (FIGS. 28 and 29) positioned side-by-side defining a center protrusion 70. Both the downwardly tapering grooves 68 having tapering lens guiding surfaces 66a and center protrusion 70 having tapering lens guiding surface 66b taper in such a manner as to close down the cross-sectional size of the open passageway 45a through the lens cartridge 38.

The sleeve portion 40 is preferably installed in the lens injecting device 12 prior to the lens cartridge 38 containing a deformable intraocular lens is inserted into the lens injecting device 12. Specifically, the fully assembled lens injecting device 12 includes the sleeve portion 40. The sleeve portion 40 can be permanently assembled to the lens injecting device 12, for example by adhesive and/or locking tabs, or can be releasably disposed within the lens cartridge assembly receiver 18. In this configuration, the sleeve portion 40 functions as a lens cartridge receiver for the lens cartridge 38.

Alternatively, the lens cartridge 38 can be inserted into the sleeve portion 40, prior to the sleeve portion 40 being installed into the lens injecting device 12.

Figures 30, 31:
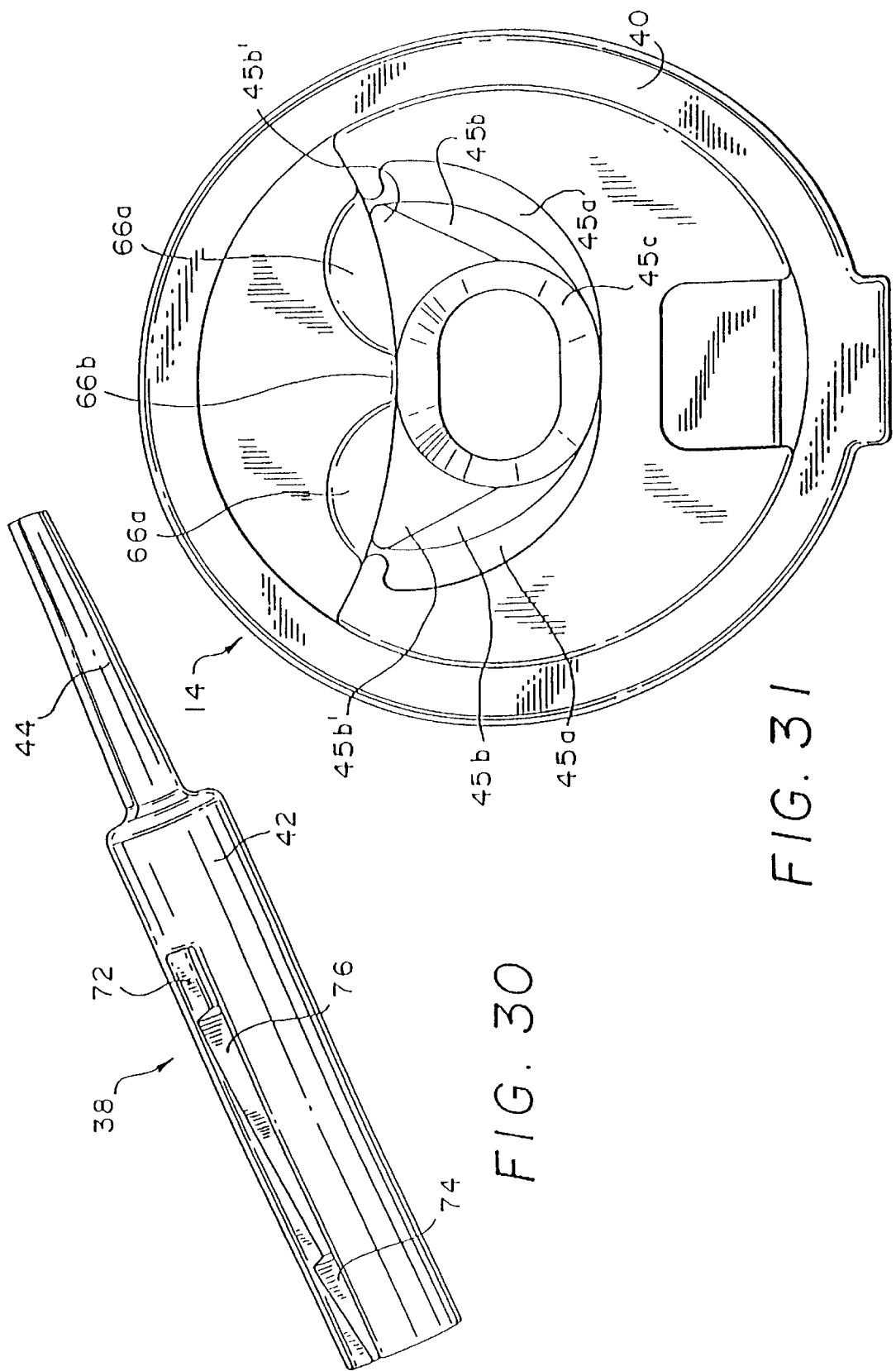
FIG. 30 is another perspective view of the lens holding portion showing the longitudinal groove in the wall of the lens holding portion with a pair of ramp catches.
FIG. 31 is an end elevational view of the preferred lens cartridge shown in FIG. 17 revealing the detailed configuration of the lens guiding surfaces inside the lens cartridge.

An outer portion of the lens cartridge 38 is provided with a longitudinal groove 72 having a pair of engaging ramp type catches 74 and 76 located in the groove 72, as shown in FIG. 30. The ramp type catches 74 and 76 cooperated with the catch 61 of the cantilever spring 60 of the sleeve portion 40 to lock the lens cartridge 38 into the lens injecting device 12 at two different locations.

The detailed configuration of the lens guiding surfaces inside the lens cartridge 38 is shown in FIG. 31 from the rear of the lens cartridge 38.

Figure 32:
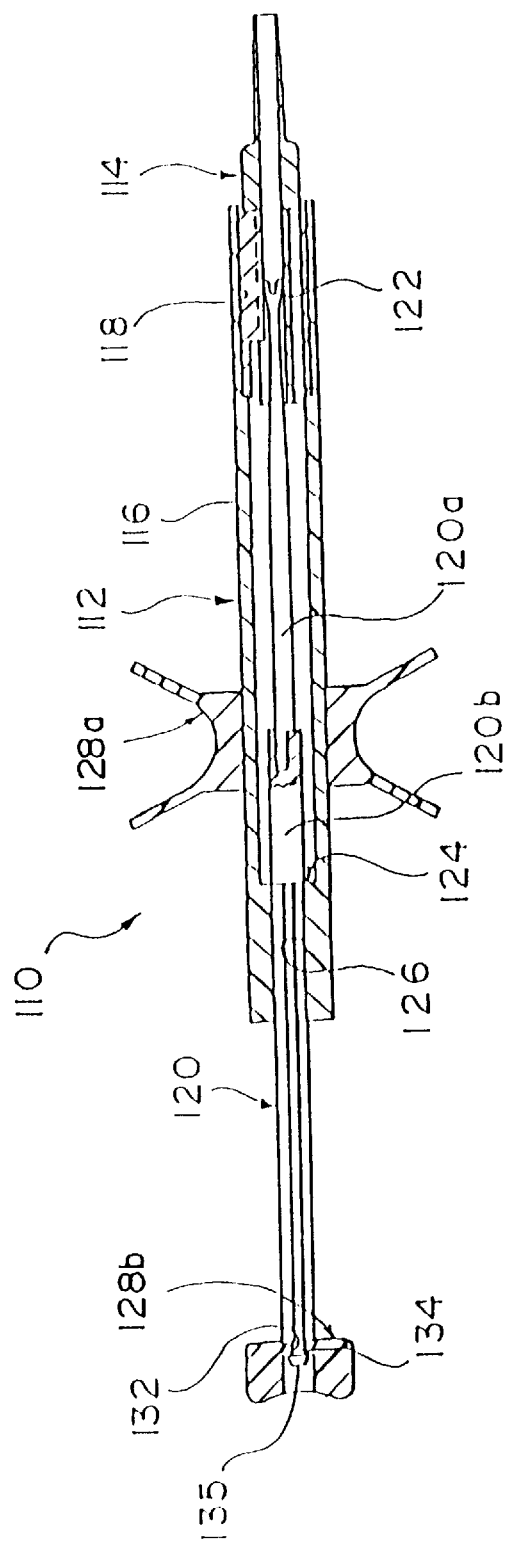
FIG. 32 is a longitudinal cross-sectional view of another embodiment of a lens injecting device according to the present invention.
Figure 43:
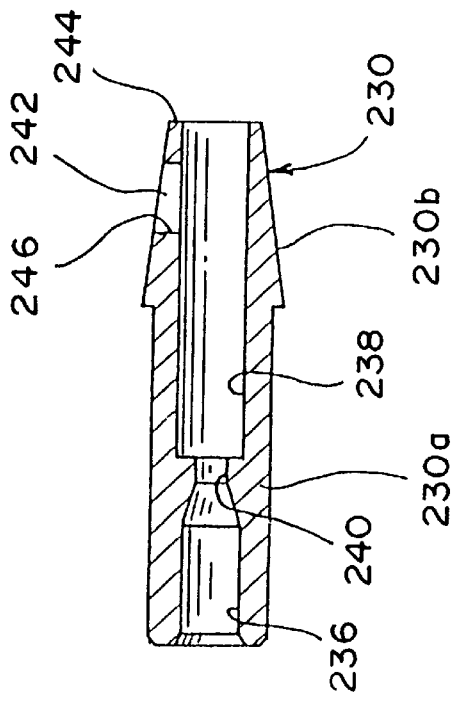
FIG. 43 is a longitudinal side cross-sectional view of the locking portion, as shown in FIG. 42.

Another embodiment of the lens injecting device 110 is shown in FIG. 32. This embodiment is provided with an a fingertip gripping device 128a and a thumb gripping device 128b, as shown to enhance manipulating and using the device.

The present invention includes the concept of pre-loading the deformable intraocular lens into the deformable intraocular lens insertion system or a portion of the deformable intraocular lens insertion system (e.g. lens cartridge). Specifically, a potentially preferred method of making and selling deformable intraocular lens is to pre-load the deformable intraocular lens in the deformable intraocular lens insertion system for purposes of storage and shipment. For example, the deformable intraocular lens can be manufactured, and then placed inside the lens injecting device or lens cartridge (i.e. inside deformable intraocular lens insertion system) prior to being packaged and shipped to a customer. This method reduces the amount of packaging by not requiring separate packages for the deformable intraocular lens and the lens cartridge and/or lens injecting device. Further, the lens cartridge and/or lens injecting device protects the deformable intraocular lens during the process of packaging, shipping and other handling, and eliminates the step of loading the deformable intraocular lens into the lens cartridge and/or lens injecting device that could potentially cause damage thereto.

This method would allow the lens cartridge and/or lens injecting device and pre-loaded deformable intraocular lens to be autoclaved together prior to insertion of the deformable intraocular lens.

BAYONET TYPE INSERTION SYSTEM

Another preferred embodiment of the deformable intraocular lens insertion system 210 according to the present invention is shown in FIG. 33. The deformable intraocular lens insertion system 210 comprises two main components including a lens injecting device 212 and a lens cartridge assembly 214.

The lens injecting device 212 comprises a cylindrical barrel 216 having a lens cartridge receiver 218 located at one end thereof, as shown in FIG. 36. The cylindrical barrel 216 can have other suitable cross-sectional shapes, however, a cylindrical-shaped barrel is particularly suitable for making, assembling, and utilizing the lens injecting device 212. The lens cartridge receiver 218 accommodates the lens cartridge assembly 214, which is securely connected to the lens injecting device 212 when inserted into the lens cartridge receiver 218, and then rotated. The important feature of this particular embodiment involves the locking arrangement between the lens cartridge assembly 214 and the lens injecting device 212, which locking arrangement will be discussed in detail below.

Once the lens cartridge assembly 214 is fully inserted into the lens injecting device 212, the lens cartridge assembly 214 cannot rotate by itself within the lens cartridge receiver 218 to prevent any relative movement therebetween which can detract from the manipulating characteristics of the deformable intraocular lens insertion system 210.

The design of the cylindrical barrel 216 is shown in FIG. 36. The cylindrical barrel 216 has a uniform circular cross-sectional shape and uniform wall thickness along its entire length, except for a guide portion 216a for accommodating movable plunger 220 of the device to be described in detail below.

The lens injecting device 212 further includes a movable plunger 220 disposed within the cylindrical barrel 216. The movable plunger 220 includes a manipulating tip 222 for engaging with the deformable intraocular lens for forcing the deformable intraocular lens from the loaded lens cartridge assembly 214. In the deformable intraocular insertion system 210 the movable plunger 220 comprises two movable plunger portions 220a and 220b, as shown in FIG. 36. The two movable plunger portions 220a and 220b can have a one-piece construction, or can be made as two separate pieces connected together in a suitable manner to facilitate assembly.

In the embodiment of the deformable intraocular lens insertion system 210, the movable plunger 220 is slidably disposed within the cylindrical barrel 216. Specifically, a plunger guide 224 is disposed within the cylindrical barrel 216, which plunger guide 224 is provided with a passageway 226 for slidably supporting the movable plunger 220. In the embodiment shown, the inner dimensions of the passageway 226 of the plunger guide 224 are slightly greater than the outer dimensions of the movable plunger 220 to provide the guide arrangement. Further, the cross-sectional shape of the passageway 226 is preferably made the same as the cross-sectional shape of the movable plunger 220 (i.e. matching shapes) to enhance close tolerance fit therebetween to improve sliding accuracy. More preferably, the cross-sectional shapes of the passageway 226 of the plunger guide 224 and the movable plunger 220 are interlocking to prevent relative rotation between the cylindrical barrel 216 fixed to the plunger guide 224 and the movable plunger 220, again to enhance the manipulating characteristics of the deformable intraocular lens insertion system 210. For example, the cross-sectional shapes of the passageway 226 of the plunger guide 224 and the movable plunger 220 can have a cross (+) shape to provide an interlocking arrangement, as shown in FIG. 37. Alternative embodiments of the movable plunger 220' and the plunger guide 224' are shown in FIG. 37A, wherein both the transverse cross-sectional shape of the movable plunger 220b' and the plunger guide 224' have a modified (+) that only allows one orientation to ensure proper assembly of the movable plunger 220b' inside the lens injecting device 212.

In the embodiment shown in FIG. 36, the plunger guide 224 is part of the cylindrical barrel 216. For example, the cylindrical barrel 216 can be injection molded of plastic to include the plunger guide 224 as a one-piece unit. Alternatively, the plunger guide 224 can be made as a separate piece, and then assembled inside the cylindrical barrel 216. Further, in the embodiments shown, the plunger guide 224 is provided at one end of the cylindrical barrel 216, however, the plunger guide 224 can be located at a position inside the cylindrical barrel 216 away from the end of the cylindrical barrel 216.

The movable plunger 220 is provided with a fingertip gripping device 228 located at an end opposite to the manipulating tip 222. The gripping device 228 is preferably connected in a freely rotating manner with the end of the movable plunger 220, however, a non-rotating type connection can also be utilized.

In the deformable intraocular lens insertion system 210, the gripping device 228 is essentially cylindrical-shaped, and includes internal threads 228a cooperating with external threads 228b of the cylindrical barrel, as shown in FIG. 36. The outer surface of the gripping device can be fluted to increase the gripping ability by a users fingertips.

The gripping device 228 can have the same construction as the gripping device 28 in the embodiment of the deformable intraocular lens insertion device 10, as shown in FIG. 2, and as explained in detail above.

The details of the locking arrangement between the lens injecting device 212 and lens cartridge assembly 214 will now be explained.

The front end of the cylindrical barrel 216 is provided with a locking portion 230, as shown in FIGS. 41 to 45. The locking portion 230 is shown as a separate piece from the cylindrical barrel 216, however, a one-piece construction is also suitable.

The locking portion 230 comprises an insert portion 230a received within the front end of the cylindrical barrel 216, and a conical portion 230b. The insert portion 230a is provided with a longitudinal rib 232, as shown in FIGS. 39 to 41 received within a groove 234 in the front end of the cylindrical barrel 216 to prevent relative rotation between the locking portion 230 and the cylindrical barrel 216 of the lens injecting device 212. The locking portion 230 is connected to the cylindrical barrel 216 by interference fit, snap-connection, adhesive, sonic welding, and/or other suitable means of connection.

The insert portion 230a includes a passageway 236 for accommodating the front movable plunger portion 220a of the movable plunger 220, and a lens cartridge receiver 238 for accommodating the lens cartridge assembly 214. A plunger guide 240 for accommodating the front movable plunger portion 220a of the movable plunger 220 is provided between the passageway 236 and lens cartridge receiver 238, as shown in FIG. 41.

The locking arrangement between the lens cartridge assembly 214 and locking portion 230 is shown in FIGS. 42 to 45.

Figure 45:
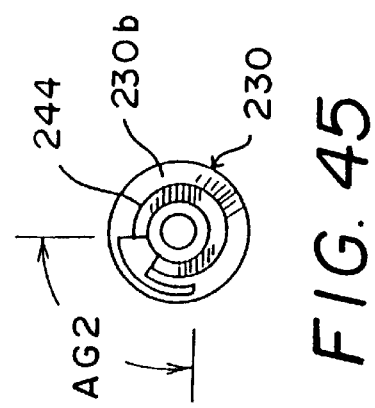
FIG. 45 is an end elevational view of the locking portion, as shown in FIG. 43.
Figure 42:
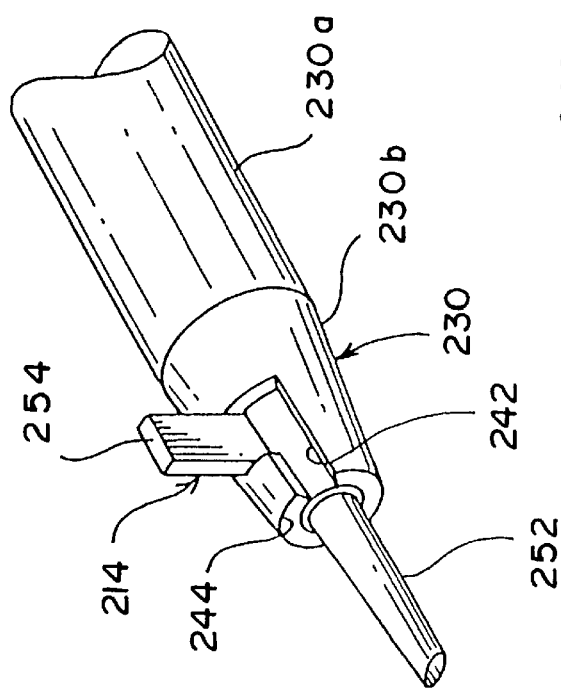
FIG. 42 is a partial perspective view of a lens cartridge fully loaded into the locking portion of the lens injecting device.
Figure 44:
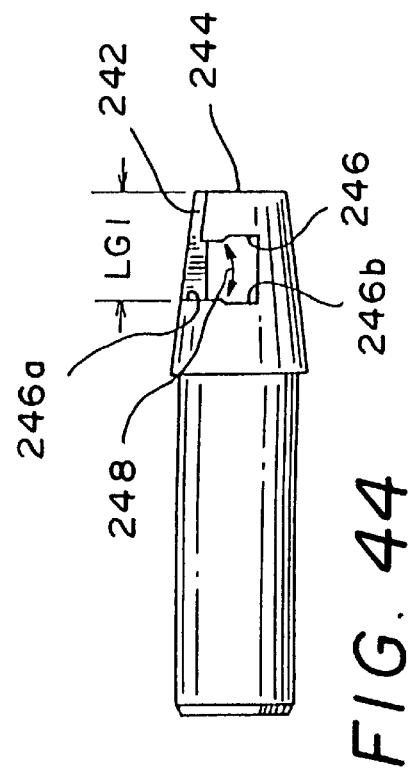
FIG. 44 is a top elevational view of the locking portion, as shown in FIG. 43.

The conical portion 230b is provided with a longitudinal slot 242 extending from a front edge 244 of the locking portion 230 rearwardly in a longitudinal direction of the deformable intraocular lens insertion system 210. The length of the slot 242 is indicated by length LG1, as shown in FIG. 44. A transverse slot 246 extends from the rear end of the longitudinal slot 242. The length of the transverse slot 246 is sufficient to allow for an approximate ninety degree (90°) angle of rotation of the lens cartridge assembly 214 inside the lens cartridge receiver 238 of the locking portion 230. The angle of rotation is indicated as AG2, as shown in FIG. 45. The transverse slot 246 includes a first transverse slot portion 246a and a second transverse slot portion 246b, as shown in FIG. 44. The second transverse slot portion 246b is slightly wider than the first transverse slot portion 246a so that a tab of the lens cartridge assembly 214 is securely locked when fully rotated to the locked position after rotating approximately ninety degrees (90°). Specifically, a set of edges 248 are defined in the transverse slot 246 by the transition between the first transverse slot portion 246a and second transverse slot portion 246b providing a set of opposed locking edges 248 providing a snap fit connection to releasably lock the tab of the lens injecting device 212 in the second transverse slot portion 246b, effectively preventing inadvertent rotation of the lens cartridge assembly 214 relative to the lens injecting device 212.

The details of the lens cartridge assembly 214 will now be explained in reference to FIGS. 46 to 49.

The lens cartridge assembly 214 comprises a lens receiving portion 250 connected to a nozzle portion 252, and the tab 254 extends from the lens receiving portion 250. The lens cartridge assembly 214 is preferably a one-piece unit made of injection molded plastic.

The lens receiving portion 250 is provided with a longitudinal slot 256 through the wall thereof leading into a lens receiving passageway 258, as shown in FIG. 46.

The passageway 258 is defined by a constant cross-sectional shape and size passageway portion 258a leading into a downwardly tapering or converging transition passageway portion 258b, leading into a downwardly tapering passageway 258c through the nozzle portion 252, as shown in FIG. 48. This configuration of the passageway portions through the lens cartridge assembly 214 is for further folding the deformable intraocular lens as it is forced through the lens cartridge by the manipulating tip, and out through the downwardly tapering passageway 258c in the nozzle portion 252 of the lens cartridge assembly 214 into a small incision through the eye. The end of the nozzle portion 252 is preferably provided with a bevel end 260.

The lens cartridge assembly 214 can be provided with a pair of guides 262 for guiding and centering the lens cartridge assembly 214 inside the lens cartridge receiver 238 of the locking portion 230.

LOADING LENS INSERTION DEVICE

A deformable intraocular lens is loaded into the lens cartridge assembly 214 by initially resting the deformable intraocular lens over the longitudinal slot 256. The center of the deformable intraocular lens is then forced downwardly, for example, with a plastic dowel or other suitable manipulating instrument until the lens is folded and moves into the lens receiving passageway 258.

Once the deformable intraocular lens is fully loaded into the lens cartridge assembly 214, the lens cartridge assembly 214 is then loaded into the lens cartridge receiver 238 of the locking portion 230 of the lens injecting device 212. Specifically, the back end of the lens cartridge assembly 214 is fitted and guided into the lens cartridge receiver 238 of the locking portion 230 with the tab 254 of the lens cartridge assembly 214 being received within the longitudinal slot 242. The lens cartridge assembly 214 is advanced rearwardly until the tab 254 of the lens cartridge assembly 214 makes contact with the rear wall 246a of the first transverse slot portion 246a acting as a stop from further rearward movement. The tab 254 of the lens cartridge assembly 214 is then rotated by pushing against one side thereof in the direction of rotation until the lens cartridge assembly 214 is rotated so that the tab 254 snaps into the second transverse slot portion 246b, effectively locking the lens cartridge assembly 214 from rotation relative to the lens injecting device 212. Then, the movable plunger 220 is actuated by the gripping device 228 to force the manipulating tip 222 into the lens cartridge assembly 214, and then force the deformable intraocular lens from the lens cartridge assembly 214 through the nozzle portion into the eye.

We claim:

1. A deformable intraocular lens insertion system for inserting a deformable intraocular lens into an eye, comprising:
    a lens cartridge for accommodating the deformable intraocular lens, said lens cartridge including a lens receiving portion connected to a nozzle portion;
    a lens injecting device having a lens cartridge receiver, said lens injecting device including a barrel with a locking portion located at one end of said barrel, said lens injecting device including a plunger movably disposed within said barrel; and
    a rotary connecting arrangement for connecting said lens cartridge in said lens cartridge receiver of said lens injecting device upon inserting said lens cartridge in said lens cartridge receiver of said lens injecting device, and then rotating said lens cartridge relative to said lens injecting device, said rotary connecting arrangement being defined by a longitudinal slot leading to a transverse slot in said locking portion, and said lens cartridge including a tab for cooperating with said longitudinal slot and said transverse slot to lock said lens cartridge in said lens cartridge receiver of said lens injecting device, said tab of said lens cartridge extending substantially outward a distance from said lens injecting device whereby a user can grip and rotate said tab to lock and unlock said lens cartridge within said lens cartridge receiver of said lens injecting device, said trasverse slot being defined by a first transverse slot portion leading to a second transverse slot portion, said second transverse slot portion being wider than said first transverse slot portion providing an opposed pair of locking edges in said transverse slot to prevent said lens cartridge from inadvertently rotating relative to said lens injecting device once locked into position.

2. A system according to claim 1, wherein said locking portion is a separate component from said barrel.

3. A system according to claim 2, wherein said locking portion includes an insert portion connected to a cone-shaped portion, said insert portion being received within said one end of said barrel.

4. A system according to claim 3, wherein said locking arrangement is defined by a longitudinal slot leading to a transverse slot in said cone portion of said locking portion, and said lens cartridge including a tab for cooperating with said longitudinal slot and said transverse slot to lock said lens cartridge in said lens cartridge receiver of said lens injecting device.

5. A system according to claim 3, wherein said insert portion is provided with longitudinal rib received within a longitudinal slot inside said barrel to prevent relative rotation between said locking portion and said barrel.

6. A system according to claim 2, wherein said lens injecting device is defined by a barrel and a plunger movably disposed within said barrel, said locking portion having a passageway provided with a guide for slidably supporting said plunger.

7. A system according to claim 1, wherein said locking arrangement is defined by a bayonet type locking arrangement between said lens cartridge and said lens injecting device.

8. A system according to claim 7, wherein said bayonet type locking arrangement is defined by a slot in said lens cartridge receiver of said lens injecting device cooperating with a tab on said lens cartridge, said slot configured to allow said lens cartridge to be initially loaded in a longitudinal direction of said lens injecting device, and then rotated into a fully locked position.

9. A system according to claim 1, wherein said lens cartridge is provided with a tab defining a portion of said locking arrangement.

10. A system according to claim 9, wherein said tab extends from said lens receiving portion of said lens cartridge.

11. A system according to claim 10, wherein said tab extends perpendicularly from said lens holding portion.

12. A system according to claim 9, wherein said lens cartridge includes at least one protrusion for guiding and centering said lens cartridge within said lens cartridge receiver.

13. A system according to claim 9, wherein said lens cartridge is provided with a lens receiving passageway having a fixed size and shape cross section leading to a downwardly tapering passageway for further folding the deformable intraocular lens.

14. A system according to claim 1, wherein said rotary connecting arrangement includes means for positively locking said lens cartridge from relative rotation with respect to said lens injecting device.

15. A system according to claim 14, wherein said locking means is releasable to allow said lens cartridge to be removed from said lens injecting device after being once placed in a fully locked position.

\* \* \* \* \*